(12) United States Patent
Horinek et al.

(10) Patent No.: US 9,744,381 B2
(45) Date of Patent: Aug. 29, 2017

(54) TOPICAL COMPOSITIONS AND METHODS FOR INFLUENCING ELECTROMAGNETIC RADIATION ON CUTANEOUS EXTRACELLULAR MATRIX PROTEIN PRODUCTION

(75) Inventors: David Dru Horinek, Camarillo, CA (US); James Vincent Gruber, Washington, CT (US); Vito Thomas Cataldo, Somerset, NJ (US); Robert Michael Klein, Los Angeles, CA (US)

(73) Assignee: ARCH CHEMICALS, INC., Atlanta, GA (US)

( * ) Notice: Subject to any disclaimer, the term of this patent is extended or adjusted under 35 U.S.C. 154(b) by 375 days.

(21) Appl. No.: 13/506,023

(22) Filed: Mar. 21, 2012

(65) Prior Publication Data
US 2012/0263807 A1    Oct. 18, 2012

Related U.S. Application Data

(60) Provisional application No. 61/469,149, filed on Mar. 30, 2011.

(51) Int. Cl.
| | | |
|---|---|---|
| *A01N 65/00* | (2009.01) | |
| *A61Q 19/00* | (2006.01) | |
| *A61K 8/44* | (2006.01) | |
| *A61K 8/97* | (2017.01) | |
| *A61K 8/49* | (2006.01) | |
| *A61Q 17/04* | (2006.01) | |
| *A61K 8/99* | (2017.01) | |
| *A61K 8/02* | (2006.01) | |
| *A61Q 1/06* | (2006.01) | |
| *A61Q 1/08* | (2006.01) | |
| *A61Q 19/10* | (2006.01) | |

(52) U.S. Cl.
CPC .............. *A61Q 19/00* (2013.01); *A61K 8/022* (2013.01); *A61K 8/44* (2013.01); *A61K 8/442* (2013.01); *A61K 8/4913* (2013.01); *A61K 8/97* (2013.01); *A61K 8/99* (2013.01); *A61Q 17/04* (2013.01); *A61Q 1/06* (2013.01); *A61Q 1/08* (2013.01); *A61Q 19/10* (2013.01)

(58) Field of Classification Search
CPC .................................................. A61K 36/00
USPC ........................................................ 424/725
See application file for complete search history.

(56) References Cited

U.S. PATENT DOCUMENTS

| | | | | |
|---|---|---|---|---|
| 6,514,487 | B1 * | 2/2003 | Barr ................................ | 424/65 |
| 7,846,452 | B2 * | 12/2010 | Pasco et al. ............. | 424/195.17 |
| 2006/0198810 | A1 | 9/2006 | Murray et al. | |
| 2006/0210621 | A1 * | 9/2006 | Mower .......................... | 424/451 |
| 2007/0065396 | A1 | 3/2007 | Morariu | |
| 2009/0208431 | A1 | 8/2009 | Bommarito | |
| 2010/0291050 | A1 * | 11/2010 | Daikeler et al. ........... | 424/93.44 |

FOREIGN PATENT DOCUMENTS

| | | |
|---|---|---|
| FR | 2930154 A1 | 10/2009 |
| WO | 0024369 A1 | 5/2000 |
| WO | 2009141542 | 11/2009 |
| ZA | 9904696 | * 4/2000 |

OTHER PUBLICATIONS

Olivier Potterat, "Goji (*Lycium barbarum* and *L. chinense*): Phytochemistry, Pharmacology and Safety in the Perspective of Traditional Uses and Recent Popularity", Planta Medica, vol. 76, No. 01, Jan. 1, 2010 (Jan. 1, 2010), pp. 7-19, XP55036716.

* cited by examiner

*Primary Examiner* — Michael Meller
(74) *Attorney, Agent, or Firm* — McBee Moore Woodward & Vanik IP, LLC

(57) ABSTRACT

Disclosed herein is a composition that is suitable for influencing electromagnetic radiation on cutaneous extracellular matrix protein production. The composition contains (a) a proanthrocyanin, a polyphenol or a proanthrocyanin/polyphenol-containing plant extract, absorbed or adsorbed onto an inert carrier, where component (a) is responsive to UV, IR or visible light; (b) a photo-activatable amino acid or amino acids blend; and (c) a dermatologically-acceptable vehicle, wherein component (a) is present in an amount of from about 15 wt % to about 35 wt % based on the total amount of component (a) and component (b), said component (b) is present in an amount of from about 65 wt % to about 85 wt % based on the total amount of component (a) and component (b), and said component (c) is present in an amount of from about 90 wt % to about 99.95 wt % based on the total weight of the composition.

11 Claims, 4 Drawing Sheets
(1 of 4 Drawing Sheet(s) Filed in Color)

TOPICAL COMPOSITIONS AND METHODS FOR INFLUENCING ELECTROMAGNETIC RADIATION ON CUTANEOUS EXTRACELLULAR MATRIX PROTEIN PRODUCTION

CROSS REFERENCE TO RELATED APPLICATIONS

This application claims priority to U.S. provisional Application No. 61/469,149 filed Mar. 30, 2011, which is incorporated herein by reference in its entirety.

FIELD OF THE INVENTION

The present invention relates to topical compositions and methods for using these compositions for influencing electromagnetic radiation on cutaneous extracellular matrix protein production.

BACKGROUND OF THE INVENTION

Energy in the form of light can cause deleterious effects on the skin. For example, exposure to sunlight prematurely ages the skin. Exposure to UV light is responsible for the wrinkles, irregular pigmentation, redness, leathery, rough texture and weathered skin attributable to sun exposure. In addition, excessive sun exposure may increase the risk of skin cancers.

In order to minimize the damaging effect of the sun on the skin, one may choose to avoid sun exposure or use sunscreens to block sun's UV radiation from contacting the skin. However, in doing so one may inadvertently diminish the skin's ability to perform critical biochemical processes dependent on sunlight such as the manufacture of Vitamin D precursors.

Efforts have been made to transform the energy the skin absorbs in a positive fashion for beneficial use in biochemical processes. Illustratively, it has been disclosed that application of laser pulse light or light-emitting diode arrays in combination with various photosensitizers could accelerate the healing of wounds and tumors in animals and humans. See Whelan HT et al., Space Tech and App International Forum 458; 3-15:1999.

U.S. Pat. No. 7,074,499 discloses that fabric products incorporating an optically-responsive powder may provide beneficial properties to the skin and body of the subject wearing such a product. According to the patentees, the active materials for the powder include silicon, carbon, and various vitreous glasses, such as oxides of aluminum, titanium, silicon, boron, calcium, sodium, and lithium.

Recently, Huang P J et al. disclosed the use of a copper-containing peptide to improve the wound healing benefits of monochromatic red light. (Juang P J et al., Phytomed and Las Surg 25 (2007) 183-190).

Bruce M. Freedman disclosed that the topical application of polyphenolic antioxidants during intense pulsed light (IPL) treatment therapy enhances the effects of IPL treatment. See Journal of Cosmetic Dermatology, 8(4):254-259, 2009. However, according to the article, the antioxidants had to be delivered to the skin via aggressive means such as a crystal-free microdermabrasion technique immediately prior to each IPL treatment and also between IPL treatments.

Despite these purported advances, a need still exists for a novel composition that is effective to interact with light energy to provide a beneficial effect to the skin while at the same time is not constrained by enclosure in polymeric fibers or requires aggressive dermal abrasion techniques for its delivery. The present invention provides one answer to that need.

SUMMARY OF THE INVENTION

In one aspect, the present invention provides a powder comprising (a) a proanthrocyanin, a polyphenol or a proanthrocyanin/polyphenol-containing plant extract, absorbed or adsorbed onto an inert carrier, said component (a) being responsive to UV, IR or visible light; and (b) a photo-activatable amino acid or amino acids blend, wherein component (a) is present in an amount of from about 15 wt % to 35 wt %, and component (b) is present in an amount of from about 65 wt % to about 85 wt %, all based on the total weight of the powder.

In another aspect, the present invention provides a topical composition effective for influencing electromagnetic radiation on cutaneous extracellular matrix protein production. The composition contains (a) a proanthrocyanin, a polyphenol or a proanthrocyanin/polyphenol-containing plant extract, absorbed or adsorbed onto an inert carrier, (b) a photo-activatable amino acid or amino acids blend; and (c) a dermatologically-acceptable vehicle, wherein component (a) of the composition is responsive to UV, IR or visible light.

In the topical composition, component (a) is present in an amount of from about 15 wt % to about 35 wt % based on the total amount of component (a) and component (b), component (b) is present in an amount of from about 65 wt % to about 85 wt % based on the total amount of component (a) and component (b), and component (c) is present in an amount of from about 90 wt % to about 99.95 wt % based on the total weight of the composition.

In another aspect, the present invention relates to a method for influencing the effect of electromagnetic radiation on the skin by causing cutaneous extracellular matrix production on the skin. The method includes topically applying the above described topical composition to the skin before or during the time the skin is exposed to the electromagnetic radiation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
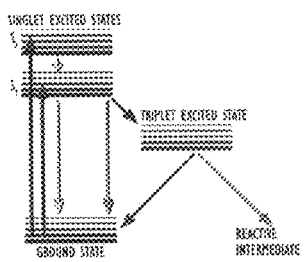
FIG. 1 is a Jablonski Diagram showing excitation of electrons and relaxation with release of fluorescence and/or phosphorescence.

The present inventors surprisingly found that a blend of (a) certain polyphenols, proanthrocyanins or their combinations and (b) an amino acid or amino acids blend, provides enhanced benefits in extracellular matrix expression after topically applied to the skin before or during the skin is exposed to UV, IR or visible light as compared to either component (a) or component (b) used alone.

Without wishing to be bound by any particular theory, it is believed that UV, IR or visible light interacts with certain proanthrocyanin/polyphenolic compounds to elicit a shift in the wavelength of the light. It is further believed that the resulting modified light then activates certain radiation labile amino acids, which in turn are able to more readily react with the amino acids naturally present in the skin, or perhaps can penetrate more deeply into the lower layers of the skin thus promoting accelerated formation of critical extracellular matrix proteins, in particular, fibronectin and elastin. It is also hypothesized that the modified light might stimulate metabolism in skin cells, which in combination with the amino acids may accelerate the reconstruction of extracellular matrix proteins such as collagen, elastin and the like.

The terms "interaction" and "interacting" as used in the context of the present invention mean that absorbing, reflecting, and/or changing the wavelength of the UV, IR or visible light. For example, the high or aggressive radiation, such as ultraviolet radiation is transformed to a lower energy fluorescence and/or phosphorescence via well-known processes. These processes are shown diagrammatically in the figure below known as a Jablonski Diagram. The diagram shows how higher orbital electrons in the polyphenols are excited by UV, visible or infrared radiation and then relieve this absorbed radiation in a stepwise process that results in the release of a lower energy fluorescence or phosphorescence. Advantageously, the process of radiation absorption, conversion and release (emission) is referred to as interaction or interacting.

Accordingly, in one embodiment, the present invention provides a powder containing: (a) a proanthrocyanin, a polyphenol or a proanthrocyanin/polyphenol-containing plant extract, absorbed or adsorbed onto an inert carrier, (b) a photo-activatable amino acid or amino acids blend; and (c) a dermatologically-acceptable carrier, wherein component (a) is responsive to UV, IR or visible light.

In the powder, component (a) is present in an amount of from about 15 wt % to 35 wt %, preferably about 15 wt % to about 25 wt %, more preferably about 20 wt %, and component (b) is present in an amount of from about 65 wt % to about 85 wt %, preferably from about 70 wt % to about 85 wt %, more preferably about 80 wt %, all based on the total weight of the powder.

Component (a) of the powder can be a proanthrocyanin, a polyphenol or a proanthrocyanin/polyphenol-containing plant extract, or combinations thereof which is responsive to electromagnetic radiation such as UV, IR or visible light. As used herein, "responsive" means interacting with UV, IR or visible light by absorbing, reflecting, and/or changing the wavelength of UV, IR or visible light.

In one embodiment, the proanthrocyanin, polyphenol or their combination is derived principally, but not necessarily exclusively, from plants such as acai, green tea, capsasin and the like. Exemplary suitable proanthrocyanin/polyphenol-containing plant extracts include, but are not limited to, curcuma extracts, safflower extracts, capsicum extracts, acai extracts, *morinda citrifolia* extracts, and combinations thereof.

Extraction of the polyphenols and proanthrocyanins from plants can be done using any methods known to those skilled in the art. Exemplary methods include solvent extraction, super critical fluid extraction, steam extraction and the like.

It is also appreciated that polyphenols and proanthrocyanins could be synthetically-derived instead of naturally-derived although proanthrocyanins and polyphenols from natural sources are preferred.

Preferably, the proanthrocyanins, polyphenols, or proanthrocyanins/polyphenol plant extracts are absorbed or adsorbed onto an inert carrier. It is hypothesized that the employment of an inert carrier allows better deposition of the proanthrocyanins, polyphenols and proanthrocyanins/polyphenol-containing plant extracts onto the skin than would occur with direct mixing of these ingredients into a skin care formulation. However, use of the inert carrier is not strictly required for the purposes of the present invention. The proanthrocyanins, polyphenols, and proanthrocyanins/polyphenol-containing plant extracts could potentially be added directly to a formulation without attachment to the inert carrier to achieve the same beneficial effects when used in combination with suitable amino acids.

The inert carrier can be any of the common minerals suitable for use in topical applications. Of particular interest are mineral powders such as, for example, silicone dioxide, titanium dioxide, zinc oxide, magnesium oxide, tricalcium phosphate and calcium pentaphosphate and the like. In one embodiment, the inert carrier used in the composition of the invention is tricalcium phosphate.

The methods to coat the inert carrier with the proanthrocyanins, polyphenols and/proanthrocyanins/polyphenol-containing plant extracts through either absorption (penetrated coating) or adsorption (surface coating) are not particularly limited. Preferably, proanthrocyanins, polyphenols and proanthrocyanins/polyphenol-containing plant extracts are coated in such a way that they will remain intact on the inert carrier even in the environment of a cosmetic or personal care product. Suitable processes include fluid bed coating, spray drying, filtration and various other processes of encapsulation known to those skilled in the art. In one embodiment, suitable plant extracts are mixed with the inert carrier to provide a mixture. The mixture is subsequently filtered and the solid obtained is dried thereby providing component (a).

Preferably, the weight ratio of the inert carrier to the proanthrocyanins, polyphenols or proanthrocyanin/polyphenol-containing plant extracts is between about 70:30 and about 99:1, preferably between about 80:20 and about 95:5, more preferably between about 85:15 and about 95:5.

Component (b) of the composition of the invention is a photo-activatable amino acid or a blend of amino acids. It can be photo-activated when used in combination with proanthrocyanins, polyphenols or proanthrocyanins/polyphenol-containing plant extracts in the presence of UV, IR or visible light.

Suitable amino acids include, but are not limited to, the twenty naturally occurred eukaryotic amino acids. The standard amino acids include: Alanine, Cysteine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, and Tyrosine.

In a preferred embodiment, component (b) of the composition is a blend of amino acids which contains amino acids known to be responsive to light, such as for example, phenylglycine, phenylalanine, tryptophan, tyrosine and the like, and amino acids known to exist in the skin and to comprise specific extracellular matrix proteins such as, for example, glycine, lysine and proline.

The amino acids blend of the present invention can be made by physical blending of the individual amino acids or by extracting amino acids from a natural source. In one embodiment, component (b) is a blend of Betaine, Alanine, Glutamic acid, Proline, Hydroxyproline, Arginine, Aspartic acid and Serin. In another embodiment, component (b) is a blend of amino acids isolated from the plant Wolfberry (*Lycium barbarum*), advantageously fruit of Wolfberry. In yet another embodiment, component (b) is a blend of amino acids derived from yeasts.

The powder of the present invention can be readily incorporated into a topical composition. Accordingly, in one embodiment, the present invention provides a topical composition containing (a) a proanthrocyanin, a polyphenol or a proanthrocyanin/polyphenol-containing plant extract, absorbed or adsorbed onto an inert carrier, said component (a) being responsive to UV, IR or visible light; (b) a photo-activatable amino acid or amino acids blend; and (c) a dermatologically-acceptable vehicle, wherein said component (a) is present in an amount of from about 15 wt % to about 35 wt % based on the total amount of component (a) and component (b), said component (b) is present in an amount of from about 65 wt % to about 85 wt % based on the total amount of component (a) and component (b), and said component (c) is present in an amount of from about 90 wt % to about 99.95 wt % based on the total weight of the composition.

Component (a) and (b) have been described above in the context of the powder of the invention. Component (c) of the composition of the invention is a dermatologically acceptable vehicle. The phrase "dermatologically-acceptable vehicle", as used herein, means that the carrier is suitable for topical application to the skin, has good aesthetic properties, is compatible with the actives of the present invention and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references: "Sun Products Formulary" Cosmetics & Toiletries, vol. 105, pp. 122-139 (Dec. 1990); "Sun Products Formulary", Cosmetics & Toiletries, vol. 102, pp. 117-136 (Mar. 1987); U.S. Pat. No. 4,960,764 to Figueroa et al., issued Oct. 2, 1990; and U.S. Pat. No. 4,254,105 to Fukuda et al., issued Mar. 3, 1981.

A more detailed discussion of suitable vehicles is found in U.S. Pat. No. 5,605,894 issued to Blank et al., and, U.S. Pat. No. 5,681,852 to Bissett. The carrier can also be a powdered-type topical composition such as, for example, a powdered foundation.

The topical compositions of the present invention may optionally comprise additional skin actives. Non-limiting examples of such skin actives include vitamin B3 compounds such as those described in PCT application WO 97/39733, published Oct. 30, 1997, to Oblong et al.; hydroxy acids such as salicylic acid; exfoliation or desquamatory agents such as zwitterionic surfactants; sunscreens such as 2-ethylhexyl-p-methoxycinnamate, 4,4'-t-butyl methoxy-dibenzoyl-methane, octocrylene, phenyl benzimidazole sulfonic acid; sun-blocks such as zinc oxide and titanium dioxide; anti-inflammatory agents; anti-oxidants/radical scavengers such as tocopherol and esters thereof; metal chelators, especially iron chelators; retinoids such as retinol, retinyl palmitate, retinyl acetate, retinyl propionate, and retinal; N-acetyl-L-cysteine and derivatives thereof; hydroxy acids such as glycolic acid; keto acids such as pyruvic acid; benzofuran derivatives; depilatory agents (e.g., sulfhydryl compounds); skin lightening agents (e.g., arbutin, kojic acid, hydroquinone, ascorbic acid and derivatives such as ascorbyl phosphate salts, placental extract, and the like); anti-cellulite agents (e.g., caffeine, theophylline); moisturizing agents; anti-microbial agents; anti-androgens; and skin protectants. Mixtures of any of the above mentioned skin actives may also be used. A more detailed description of these actives is found in U.S. Pat. No. 5,605,894 to Blank et al. Preferred skin actives include hydroxy acids such as salicylic acid, sunscreen, antioxidants and mixtures thereof.

Other conventional skin care product additives may also be included in the compositions of the present invention. For example, urea, guanidine, glycerol, petrolatum, mineral oil, sugar esters and polyesters, polyolefins, methyl isostearate, ethyl isostearate, cetyl ricinoleate, isononyl isononanoate, isohexadecane, lanolin, lanolin esters, cholesterol, pyrrolidone carboxylic acid/salt (PCA), trimethyl glycine (betaine), tranexamic acid, amino acids (e.g., serine, alanine, threonine, histidine) and/or their salts, panthenol and its derivatives, collagen, hyaluronic acid, elastin, hydrolysates, primrose oil, jojoba oil, epidermal growth factor, soybean saponins, mucopolysaccharides, and mixtures thereof may be used. Other suitable additives or skin actives are discussed in further detail in PCT application WO 97/39733, published Oct. 30, 1997, to Oblong et al.

The topical composition also can comprise other components that may be chosen depending on the carrier, optional components or the intended use of the formulation. Additional components include, but are not limited to antioxidants (such as BHT); emulsion stabilizers (such as carbomer); preservatives (such as phenoxyethanol); fragrances (such as pinene); humectants (such as glycerine); water-proofing agents (such as Fomblins perflouorethers); water-soluble film formers (such as hydroxypropyl methylecellulose); oil-soluble film formers (such as hydrogenated C-9 resins); moisturizing agents (such as cholesterol); cationic polymers (such as Polyquaternium-10); anionic polymers (such as xanthan gum); vitamins (such as tocopherol); and the like.

The topical composition can also encompass one or more additional active components, and as such can be either cosmetic or pharmaceutical compositions. Examples of useful actives include, but are not limited to, those that improve or eradicate age spots, keratoses and wrinkles, analgesics, anesthetics, anti-acne agents, antibacterials, antifungals, antiviral agents, antidandruff agents, antidermatitis agents, antipruritic agents, antiemetics, antihyperkeratolytic agents, anti-dry skin agents, antiperspirants, antipsoriatic agents, antiseborrheic agents, antiaging agents, antiwrinkle agents, antihistamine agents, sunscreen agents, depigmentating agents, wound-healing agents, anti-inflammatory agents, tanning agents, or hormones.

Particularly preferred embodiments of the present formulations are skin care lotions or creams. To that end, the present formulations are combined with agents that are moisturizers, emollients or humectants. Examples of useful combinations are oils, fats, waxes, esters, fatty acid alcohols, fatty acid ethoxylates, glycols, sugars, hyaluronic acid and hyaluronates, dimethicone, cyclomethicone, and the like. Further examples can be found in the International Cosmetic Ingredient Dictionary CTFA, Tenth Edition, 2004.

When exposed to UV, IR or visible light after application to the skin, the light-sensitive composition of the invention stimulates the production of critical cutaneous extracellular proteins such as collagen, elastin, fibronectin, filamentous-actin (F-actin) and the like as well as various glucosaminoglycans including hyaluronic acid and chondrotin sulfate, that are beneficial to the skin. The photoresponsive composition may also influence cellular metabolism, such as, for example, increased ATP production.

In another embodiment, the present invention is directed to a method for influencing the effect of light energy on the skin by causing cutaneous extracellular matrix production on the skin. The method includes topically applying the above described composition alone or in combination with UV, IR or visible light exposure, advantageously UV or IR exposure. The UV, IR or visible light exposure may occur before, during or after treatment with the topical compositions of the invention. In a preferred embodiment, the UV, IR or visible light exposure occurs simultaneously with or after the composition treatment.

As used herein, Ultraviolet (UV) light has wavelengths from 10 nm to 390 nm and is divided into near (390 to 300 nm), mid (300 to 200 nm) and far (200 to 10 nm) spectra regions. Visible light is a small band in the electromagnetic spectrum with wavelengths between 390 and 770 nm and is divided into violet, blue, green, yellow, orange, and red light. Infrared (IR) light spans 770 nm to 1060 nm.

The following examples are intended to illustrate, but in no way limit the scope of the present invention. All parts and percentages are by weight and all temperatures are in degrees Celsius unless explicitly stated otherwise. All the publications and the US patents referred to in the application are hereby incorporated by reference in their entireties.

EXAMPLES

Example 1

Preparation of the Proanthrocyanin/Polyphenol-Containing Plant Extracts

An extract of curcuma was made by blending 50 g of commercially available curcuma powder in 450 g of 99% anhydrous 2-propanol for 30 minutes. This blend was filtered through a 1.6 µm glass fiber filter paper and the clear liquid was collected.

By following the same method, a safflower extract, a capsicum extract and an acai extract were prepared using 50 g of safflower powder, 50 g of capsicum powder, and 50 g of acai powder respectively.

Example 2

Coating of the Mineral Powder with Proanthrocyanin/Polyphenol-Containing Plant Extracts (1) Proanthrocyanin/polyphenol-containing curcuma extract-coated mineral powder A proanthrocyanin/polyphenol-containing curcuma extract-coated mineral powder was prepared by blending 25 g of calcium triphosphate and 75 g of the curcuma extract from Example 1 for 30 minutes. The blend was filtered through a 1.6 µm glass fiber filter and the powder was dried at 40° C. in a 28 in. Hg vacuum for 4 hours to provide a powder of proanthrocyanin/polyphenol-containing curcuma extract-coated calcium triphosphate.

Figure 2:
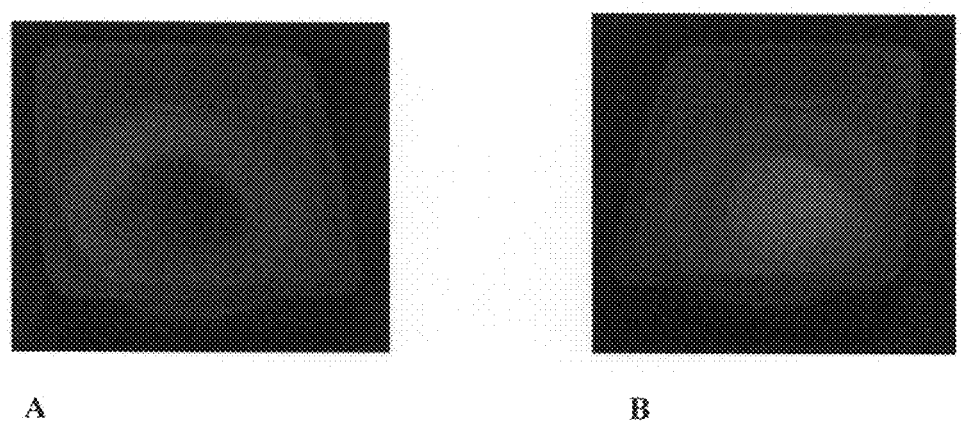
FIG. 2 shows the image of uncoated calcium triphosphate powder (A) under long wavelength UV radiation as well as the image of curcuma proanthrocyanin/polyphenol (B) coated calcium triphosphate under long wavelength UV radiation.

The uncoated calcium triphosphate powder (A) and the curcuma extract-coated calcium triphosphate (B) were examined under long wavelength UV radiation respectively. The images were shown in FIG. 2. The presence of the proanthrocyanin/polyphenol coating is demonstrated by the appearance of red fluorescent light coming off powder B under the influence of the UV light.

(2) Proanthrocyanin/polyphenol-containing safflower extract-coated mineral powder The same procedure as described in part (1) of Example 2 was followed to prepare proanthrocyanin/polyphenol-containing safflower extract-coated mineral powder using calcium triphosphate and the safflower extract from Example 1.

(3) Proanthrocyanin/polyphenol-containing capsicum extract-coated mineral powder The same procedure as described in part (1) of Example 2 was followed to prepare proanthrocyanin/polyphenol-containing capsicum extract-coated mineral powder using calcium triphosphate and the capsicum extract from Example 1.

(4) Proanthrocyanin/polyphenol-containing acai extract-coated mineral powder

A proanthrocyanin/polyphenol-containing acai extract-coated mineral powder was prepared by blending 25 g of silicon dioxide in 75 g of the acai extract from Example 1 for 30 minutes. The blend was filtered through a 1.6 µm glass fiber filter and the powder was dried at 40° C. in a 28 in. Hg vacuum for 4 hours to provide a powder of proanthrocyanin/polyphenol-containing acai extract-coated silicon dioxide.

Example 3

Blending of the Amino Acids with the Proanthrocyanin/Polyphenol-Coated Mineral Powders A blend was prepared by mixing the following proanthrocyanin/polyphenol-coated mineral powders in a ball mill at 50 rpm for 15 minutes: 10 g of curcuma proanthrocyanin/polyphenol coated mineral powder, 4 g of capsicum proanthrocyanin/polyphenol-coated mineral powder, 10 g of safflower proanthrocyanin/polyphenol-coated mineral powder and 6 g of acai proanthrocyanin/polyphenol-coated mineral powder, all prepared according to example 2, with 29.8 g of calcium carbonate, 66 g of trimethyl glycine (Betaine), 26 g of alanine, 16 g of glutamic acid, 8 g of proline, 0.2 g of hydroxyproline, 8 g of arginine, 8 g of aspartic acid, and 8 g of serine. The blend was then sifted through a 50 µm sieve and collected.

Example 4

Blending of Plant Amino Acids with the Proanthrocyanin/Polyphenol-Coated Mineral Powders In a similar fashion as described above in example 3, the proanthrocyanin/polyphenol-coated mineral powders as described in Example 3 were blended with a commercially available composition of amino acids derived from Wolfberry fruit.

Example 5

Blending of Yeast Amino Acids with the Proanthrocyanin/Polyphenol-Coated Mineral Powders In a similar fashion as described above in example 3, the proanthrocyanin/polyphenol-coated mineral powders as described in Example 3 were blended with a commercially available composition of amino acids derived from a yeast.

Example 6

In Vitro Examination of the Effect of the Composition from Example 4 on Skin Tissue Under a Monochromatic Red Light Source Using standard tissue culturing methods, Epiderm Full Thickness tissue was treated with various control powders and with the powders from Example 4. The treatment was done once a day for four days and the light energy was applied immediately after the tissues were treated with the various powders. The test samples included:
1. Untreated tissues exposed to monochromatic red light (control);
2. Tissues topically treated with 1 and 2% aqueous dispersion of a control powder, and exposed to monochromatic red light (placebo control), wherein the control powder refers to a blend of tricalcium phosphate with the amino acid blend as described in Example 4, wherein the tricalcium phosphate mineral is not coated with any proanthrocyanin/polyphenol;
3. Tissues topically treated with 1 and 2% aqueous dispersion of the composition from example 4, and exposed to monochromatic red light.

After completion of the four day treatment regime, the tissues were analyzed for expression of the extracellular protein fibronectin. Data from these studies is shown in FIG. 3.

Figure 3:
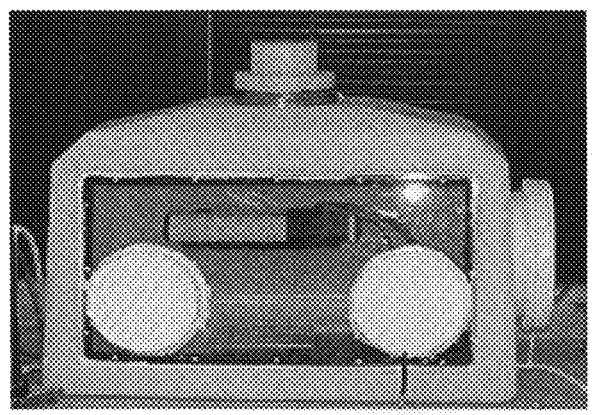
FIG. 3 is a graph showing the effect of the composition of the invention on skin tissues under a monochromatic red light source.

The data in FIG. 3 demonstrates that the proanthrocyanin/polyphenol-coating provides an increase in the expression of fibronectin, as measured by the relative optical density increase in the protein assay, in a dose-dependent fashion as compared to the placebo-control powder where the proanthrocyanin/polyphenol coating is not present.

Example 7

In Vitro Examination of the Effect of the Composition from Example 5 on Skin Tissue Under a UVB Light Source in the Presence of a Sunscreen Blend Using the same chamber shown above in Example 6, the light source was switched to a UVB light source. The treatment criteria were similar to that described in Example 6 except that the tissues were exposed to UVB light instead of monochromatic red light. Because tissues are vulnerable to the effects of UV light, a sunscreen formulation comprised of 30% Avobenzone and 70% Octylmethoxycinnamate was first applied to the tissues. Studies were conducted first to determine the amount of sunscreen that could be applied to the tissues without changes in the tissue viability due to the presence of the sunscreen.

After determining the levels of sunscreens that could be applied, the study was conducted by applying the photoresponsive powder composition from Example 5 followed by the sunscreen blend noted above and then exposing the treated tissue to UVB radiation for the prescribed time. At the end of the testing period, the tissues were analyzed for expression of elastin, a well-established extracellular matrix protein known to improve skin firmness and strength. The results of the assays are shown in FIG. 4.

Figure 4:
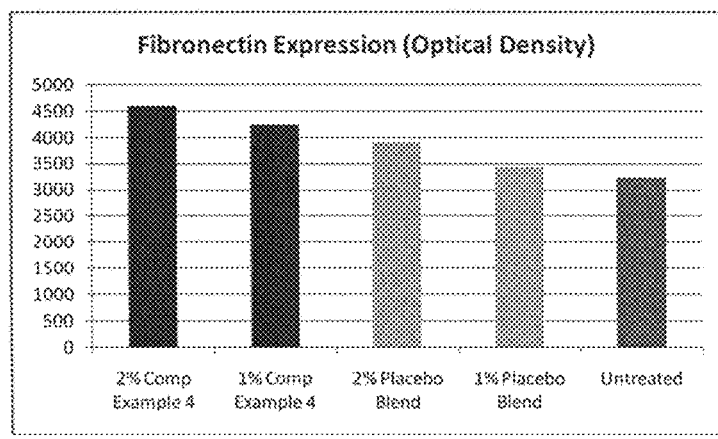
FIG. 4 is a graph showing the effect of the composition of the invention on skin tissues under a UVB light source.
Figure 5:
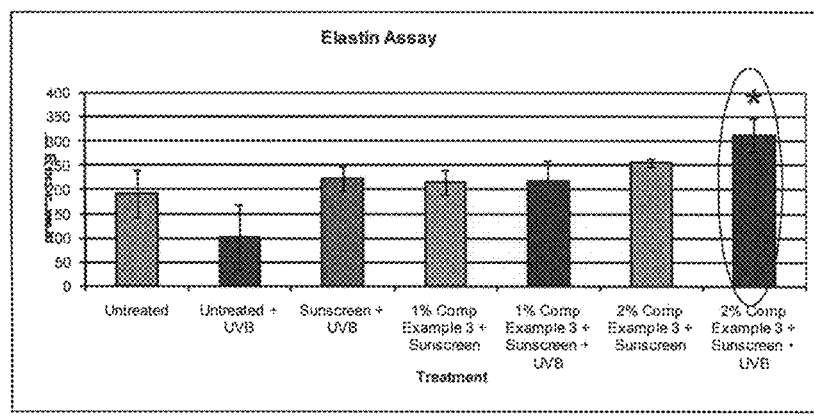

FIG. 4 demonstrates that the composition from Example 5 is able to increase elastin expression at a 2% treatment in the UVB exposed tissues significantly greater than the same powder applied but not exposed to UVB light. The data demonstrates that the combination of the proanthrocyanin/polyphenol-coated powders blended with specific amino acids provides a statistically significant increase in elastin expression due to the application of the UVB light.

The following formulations are intended to demonstrate practical formulation of the composition of the present invention into various topical vehicles. The examples are not intended to limit the scope of the claims in any way.

Example 7

Oil-in-Water Emulsion

The composition from Example 3 was formulated into an oil-in-water emulsion using the following formulation and process:

Oil in Water Emulsion Containing the Composition from Example 3

| Ingredient | INCI Nomenclature | % |
|---|---|---|
| A | | |
| Water | Water | q.s |
| Versene 100 | Tetrasodium EDTA | 0.10 |
| Glycerin | Glycerin | 2.00 |
| Carbopol Ultrez 10 | Carbomer | 0.20 |
| B | | |
| Brookswax D | Cetearyl Alcohol & Ceteareth-20 | 2.00 |
| Liquiwax DIADD** | Dioctyldodecyl Dodecanedioate | 5.00 |
| Loronate TMP-TC | Trimethylolpropane Tricaprylate/Tricaprate | 2.00 |
| Arlacel 60 | Sorbitan Stearate | 1.50 |
| Stearyl Alcohol | Stearyl alcohol | 0.20 |
| Cetyl Alcohol | Cetyl Alcohol | 0.50 |
| Stearic Acid | Stearic Acid | 0.50 |
| Myritol 318 | Caprylic/Capric Triglyceride | 2.00 |
| DC 200/100 cst | Dimethicone | 0.75 |
| C | | |
| Water | Water | 5.00 |
| TEA 99 | Triethanolamine | 0.25 |
| Composition (Example 3) | — | 1.00 |
| Mikrokill COS | Phenoxyethanol & Caprylyl Glycol & Chlorphenesin | 0.75 |

Procedure:
1. Combine Phase A and heat to 75° C. Mix until uniform.
2. Combine Phase B and heat to 75° C. Mix until uniform.
3. With slow mixing, add Phase B to Phase A. Mix for 20 minutes.
4. Add pre-mix Phase C and mix until uniform. Turn off the heat.
5. In side kettle pre-mix Phase D and add to the batch below 40° C. Mix until uniform.
6. Add Mikrokill COS and fragrance of Phase E, and mix until uniform.

Example 8

Water-in-Oil Emulsion

The composition from Example 3 was formulated into a water-in-oil emulsions using the following formulation and process:

Water in Oil Emulsion Containing Composition from Example 3

| Ingredient | INCI Nomenclature | % |
|---|---|---|
| A | | |
| Water | Water | q.s to 100 |
| Glycerin | Glycerin | 3.00 |
| Sodium Chloride | Sodium Chloride | 1.00 |
| Composition (Example 3) | | 1.00 |
| Mikrokill COS | Phenoxyethanol & Caprylyl Glycol & Chlorphenesin | 0.75 |
| B | | |
| SF1328 | Cyclomethicone & Dimethicone Copolyol | 10.00 |
| SF 1202 | Cyclomethicone | 8.50 |
| Gel Base Sil | Cyclomethicone & Dimethicone | 1.50 |
| Gel Base BSM-PE | Cyclomethicone & Dimethicone & Phenyl Trimethicone & Polyethylene | 1.50 |
| | | 100.00 |

Procedure:
1. Mix all ingredients of Phase A together.
2. Combine Phase B ingredients in order shown, thoroughly mixing each component until homogeneous before adding the next ingredients.
3. Slowly add Phase A to Phase B with good mixing. Gradually increase agitation to high shear as mixture thickens. Continue agitation for 10 minutes.

Example 9

Eye Gel Composition

The Composition from Example 3 was encapsulated into a liposomal composition, then the encapsulated ingredients were incorporated into an eye gel composition using the following process:

EYE GEL Containing Composition from Example 3 Encapsulated in a Liposome

| Ingredient | INCI Nomenclature | % |
|---|---|---|
| Water | Water | Q.S |
| Carbopol Ultrez 21 | Acrylates/C10-30 Alkyl Acrylate Crosspolymer | 0.50 |
| Keltrol CG-SFT | Xanthan Gum | 0.10 |
| Butylene Glycol | Butylene Glycol | 5.00 |
| Mikrokill COS | Phenoxyethanol & Caprylyl Glycol & Chlorphenesin | 1.00 |
| Dow Corning 193 Surfactant | Dimethicone Copolyol | 0.30 |
| Disodium EDTA | Disodium EDTA | 0.10 |
| AMP 95 | Aminomethylpropanol | 0.45 |
| Liposomomal Composition (Example 3) | | 1.00 |

Procedure:
1. Disperse the Carbopol Ultrez 21 in water at 50° C. and add the Keltrol CG-SFT. Mix until uniform.
2. Add the Butylene Glycol, Mikrokill COS, AMP, EDTA and Silicone 193. Mix until uniform.
3. Add the liposome with sweep agitation at 40° C. Mix until uniform.
5. Adjust pH to 5.5 if necessary.

Example 10

Polymerically-Encapsulated Composition 3

The Composition from Example 3 was encapsulated into a polymeric matrix using the techniques outlined in US Patent Publication No. 2003/0198682 A1.

Example 11

Lipstick Composition

The Composition from Example 3 was formulated into a lipstick using the following formulation and process:

LIPSTICK Containing Composition from Example 3

| Ingredient | INCI Nomenclature | % |
|---|---|---|
| Phase (A) | | |
| Castor Oil | *Ricinus Communis* (Castor) Seed Oil | 32.45 |
| Schercemol TISC | Triisostearyl Citrate | 15.00 |
| Liquiwax PolyIPL | Stearyl PPG-3 Myristyl Ether Dimer Dilinoleate | 5.00 |
| Liquiwax PolyEFA | Octyldodecyl PPG-3 Myristyl Ether Dimer Dilinoloeate | 15.00 |
| Candelilla Wax | *Euphorbia Cerifer* (Candelilla) Wax | 6.00 |
| Ozokerite 170D | Ozokerite | 2.50 |
| Microwax SP 19 | Microcrystalline Wax | 3.50 |
| Carnauba Wax | *Copernicia cerifera* (carnauba) wax | 1.50 |
| Methylparaben | Methylparaben | 0.20 |
| Propylparaben | Propylparaben | 0.10 |
| Phase (B) | | |
| Color Grind | | |
| Red 7 Lake c19-7711 | Red 7 Lake | 0.04 |
| Red 6 Lake c19-7712 | Red 6 Lake | 0.17 |
| Red Iron Oxide A-1205 | Iron Oxides | 2.00 |
| Titanium Dioxide Ultra Fine 70110 | Titanium Dioxide | 2.00 |
| Black Iron Oxide c33-134 | Iron Oxides | 0.05 |
| Liquiwax PolyEFA* | Octyldodecyl PPG-3 Myristyl Ether Dimer Dilinoloeate | 4.44 |
| Phase (C) | | |
| Ascorbyl Palmitate | Ascorbyl Palmitate | 0.05 |
| Flamenco Red | Mica and Titanium Dioxide | 10.00 |
| Composition (Example 3) | | 1.00 |

Procedure:
1. Combine Waxes, Oils and Preservatives (Phase A) and heat to 83°-87° C.
2. Hold temperature and stir until homogeneous.
3. Drop temperature to 75°-80° C., and add Phase B; mix until homogeneous
4. Add Pearl, Composition (Example 3) and Ascorbyl Palmitate (Phase C).
5. Pour into molds.

Example 12

Toner Composition

The Composition from Example 3 was formulated into an aqueous alcoholic tonic using the following formulation and process:

Toner Containing Composition from Example 3

| Ingredient | INCI Nomenclature | % |
|---|---|---|
| Water | Water | Qs. To 100 |
| Betafin BP-20* | Betaine | 3.00 |
| Composition (Example 3) | | 1.00 |
| Witch Hazel w/14% Alcohol | Water & Ethanol & Witch Hazel | 25.00 |
| Mikrokill COS | Phenoxyethanol & Caprylyl Glycol & Chlorphenesin | 0.75 |

Procedure:
  Charge Water and add Betafin BP-20, and Example 3 Composition. Mix until uniform.
  Add Witch Hazel and Mikrokill COS, mix until uniform.

Example 13

Body Wash Composition

The Composition from Example 3 was formulated into a body wash using the following formulation and process.

Body Wash Containing Composition from Example 3

| Ingredient | INCI Nomenclature | % |
|---|---|---|
| Water | Water | Q.S |
| Hamp-ene Na2 | Disodium EDTA | 0.10 |
| Glycerin | Glycerin | 2.00 |
| Standapol WAQ-Special | Sodium Lauryl Sulfate | 30.00 |
| Standapol ES-2 | Sodium Laureth Sulfate | 25.00 |
| Cerasynt IP | Glycol Stearate & Stearic Acid & Aminomethyl Propanol | 0.50 |
| Velvetex BA-35 | Cocoamidopropyl Betaine | 7.00 |
| Cocamide MEA | Cocamide MEA | 2.00 |
| Mikrokill COS | Phenoxyethanol & Caprylyl Glycol & Chlorphenesin | 0.75 |
| Composition (Example 3) | | 1.00 |

Procedure:
1. Heat Water to 70° C. and add Disodium EDTA, Glycerin, and mix until uniform.
2. Keep temperature above 70° C. and add Standapol WAQ Special, Standapol ES-2, Cerasynt IP, Cocamide MEA, Velvetex BA-35, and mix until uniform.
3. Cool to 45° C. and add Mikrokill COS and Composition from Example 3.
4. Mix until homogenous.

Example 14

Sub-Micron Emulsion Concentrate

This example illustrates a sub-micron emulsion concentrate that contains the Composition from Example 3.

| Ingredient | Wt % |
|---|---|
| Trimethylolpropane Tricaprylate/Tricaprate | 18.0 |
| Glycerin | 8.0 |
| Cetearyl alcohol | 2.0 |
| Ceteareth 20 | 2.0 |
| Glyceryl stearate | 2.0 |
| BHT | 0.01 |
| Composition from Example 3 | 1.0 |
| Water | to 100 |

Example 15

Loose Face Powder

This example illustrates a loose face powder that contains the Composition from Example 3.

Loose Face Powder

| Ingredient - INCI Name | Quantity (%) |
|---|---|
| Phase (A) | |
| *Zea Mays* (Corn) Starch | 48.93 |
| Mica | 25.00 |
| Zinc Stearate | 3.00 |
| Magnesium Stearate | 1.00 |
| Composition Example 3 | 2.00 |
| Titanium Oxide | 0.40 |
| Boron Nitride | 13.00 |
| Iron Oxides Red | 0.07 |
| Iron Oxides Black | 0.12 |
| Iron Oxides Yellow | 0.23 |
| Phase (B) | |
| Isododecane & PPG-3 Myristyl Ether Neoheptanoate | 6.00 |
| Tocopheryl Acetate | 0.25 |
| Fragrance | q.s |

Procedure:
1. Thoroughly blend and disperse Phase A in suitable dry blend/dispersing equipment.
2. Blend Phase B ingredients until uniform.
3. Spray Phase B into pre-mixed Phase A and continue blending.
4. Pulverize and store.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims.

What we claim:
1. A personal care topical composition that is suitable for influencing electromagnetic radiation on cutaneous extracellular matrix protein production, consisting essentially of
    (a) a proanthrocyanin, a polyphenol or a proanthrocyanin/polyphenol-containing; acai extract; absorbed or adsorbed onto an inert carrier, said component (a) being responsive to UV, IR or visible light;
    (b) a photo-activatable blend of amino acids extracted from plant wolfberry, and
    (c) a dermatologically-acceptable vehicle, wherein said component (a) is present in an amount of from about 15 wt % to about 35 wt % based on the total amount of component (a) and component (b), said component (b) is present in an amount of from about 65 wt % to about 85 wt % based on the total amount of component (a) and component (b), and said component (c) is present in an amount of from about 90 wt % to about 99.95 wt % based on the total weight of the composition.

2. The composition of claim 1 wherein the inert carrier is selected from the group consisting of magnesium oxide, silicone dioxide, titanium dioxide, tricalcium phosphate, and combinations thereof.

3. The composition of claim 1 wherein the weight ratio of component (a) to component (b) is between about 70:30 and about 99:1.

4. The composition of claim 1, wherein (a) and (b) are present as powder.

5. The composition of claim 1, consisting essentially of said (a), (b), and (c), wherein the inert carrier is selected from the group consisting of magnesium oxide, silicone dioxide, titanium dioxide, tricalcium phosphate, and combinations thereof.

6. The composition of claim 1, wherein the inert carrier comprise a calcium triphosphate powder.

7. The composition of claim 4 wherein the inert carrier is selected from the group consisting of magnesium oxide, silicone dioxide, titanium dioxide, tricalcium phosphate, and combinations thereof.

8. The composition of claim 7 wherein the weight ratio of the inert carrier to said proanthrocyanin or said polyphenol or proanthrocyanin/polyphenol-containing plant extract is between about 70:30 and about 99:1.

9. A method for influencing the effect of electromagnetic radiation on the skin by causing cutaneous extracellular matrix protein production on the skin, said method comprising applying the composition of claim 1, to the skin.

10. The method of claim 9 further comprising applying visible light, ultraviolet light and monochromatic light to the skin when the composition is applied to the skin.

11. The method of claim 9 further comprising applying visible light, ultraviolet light and monochromatic light to the skin after the composition is applied to the skin.

* * * * *